United States Patent [19]
Soyama et al.

[11] Patent Number: 4,822,423
[45] Date of Patent: Apr. 18, 1989

[54] NAIL COSMETIC COMPOSITION

[75] Inventors: Yoshikazu Soyama; Kazunori Yamazaki; Chigusa Kitamura, all of Yokohama, Japan

[73] Assignee: Shiseido Company Ltd., Tokyo, Japan

[21] Appl. No.: 79,722

[22] Filed: Jul. 30, 1987

Related U.S. Application Data

[63] Continuation of Ser. No. 775,194, Sep. 12, 1985.

[30] Foreign Application Priority Data

Mar. 15, 1985 [JP] Japan ................................. 60-51941

[51] Int. Cl.$^4$ ............................................. C09G 1/16
[52] U.S. Cl. .................................. 106/5; 106/193 R; 106/195; 424/61; 424/78
[58] Field of Search .................. 106/6, 5, 191, 193 R, 106/195; 424/78, 61

[56] References Cited

U.S. PATENT DOCUMENTS 4,158,053  6/1979  Greene et al. ........................ 424/81
4,179,304 12/1979  Rossomando ....................... 106/177
4,482,538 11/1984  Davies ................................. 106/195

FOREIGN PATENT DOCUMENTS 46-43400 12/1971  Japan .
50-13336  5/1975  Japan .
58-23614  2/1983  Japan .

Primary Examiner—Amelia Burgess Yarbrough
Attorney, Agent, or Firm—Sprung Horn Kramer & Woods

[57] ABSTRACT

A nail cosmetic composition comprising 3% to 15% by weight of nitrocellulose, 3% to 15% by weight of a resin, 2% to 8% by weight of a plasticizer, 60% to 85% by weight of a solvent, 1% to 10% by weight of a matting agent, and 0.1% to 2.5% by weight of mica in the form of a leaf. This nail cosmetic composition advantageously provides an excellent mat finish without impairing the other desired characteristics, especially the peeling resistance, of the nail cosmetic composition.

1 Claim, No Drawings

NAIL COSMETIC COMPOSITION

This is a continuation of application Ser. No. 775,194, filed Sept. 12, 1985, now pending.

BACKGROUND OF THE INVENTION

1. Field of the Invention

The present invention relates to a an improved nail cosmetic composition. More specifically, it relates to a nail cosmetic composition which is easily applied to nails, has an excellent mat finish, is resistant to undesirable peeling after application and even after the elapse of a certain period of time, but can be easily removed from the nails with an enamel remover.

2. Description of the Related Art

Various nail cosmetic compositions such as nail enamels, nail enamel basecoats, and nail enamel overcoats are known in the art. In general, the nail enamels are applied to the surfaces of nails to beautify the nails. The enamel basecoat is applied to the surfaces of the nails, prior to the coating of the nail enamel, to prevent the remaining of pigments and dyes in grooves in the nails when the coated nail enamel is removed. The enamel overcoat is applied to the surfaces of the nails, after the coating of the nail enamel, to protect the coated film of nail enamel from damage such as chipping and peeling.

Conventional nail cosmetic compositions providing a good mat finish generally contain, as essential components, nitrocelluloses, resins such as alkyd resins, acryl resins, and toluenesulfonamide resins, plasticizers, solvents, and matting agents such as silica and, optionally, other conventional additives, such as pigments, dyes, and pearl essences. These types of nail cosmetic compositions have a good coatability or applicability to the nail surfaces and provide a good mat finish. However, since a matting agent such as silica is incorporated into a conventional nail cosmetic composition, peeling resistance or anti-peeling of the coated film is impaired. That is, the coated film is susceptible to peeling with the elapse of time.

Various attempts have been made to improve the peeling resistance of the coated film of nail cosmetic compositions. For example, Japanese Examined patent publication Nos. 46-43400 and 50-13336 and Japanese Unexamined patent publication No. 58-23614 propose the use of various special resins, such as alkyd resins, acrylic resins, and sulfonamide resins. However, the peeling resistance of the coated films of nail cosmetic compositions containing the above-mentioned resins is still unsatisfactory.

SUMMARY OF THE INVENTION

Accordingly, the objects of the present invention are to eliminate the above-mentioned disadvantage of conventional nail cosmetic compositions and to provide a nail cosmetic composition having an excellent mat finish without impairing the other desired characteristics, especially the peeling resistance of the nail cosmetic composition.

Other objects and advantages of the present invention will be apparent from the following description.

In accordance with the present invention, there is provided a nail cosmetic composition comprising 3% to 15% by weight of nitrocellulose, 3% to 15% by weight of a resin, 2% to 8% by weight of a plasticizer, 60% to 85% by weight of a solvent, 1% to 10% by weight of a matting agent (or flatting agent), and 0.1% to 2.5% by weight of mica in the form of a leaf.

DESCRIPTION OF THE PREFERRED EMBODIMENTS

The nitrocelluloses usable in the nail cosmetic composition of the present invention are those generally used as a film-forming ingredient in conventional nail cosmetic compositions. Examples of such nitrocelluloses are so-called nitrocellulose RS ½ second, nitrocellulose RS ¼ second, and nitrocellulose RS ⅛ second. These nitrocelluloses can be used alone or in any mixture thereof.

These nitrocelluloses, usually those having an isopropyl alcohol (IPA) wetness (or content) of 30% by weight, can be formulated into the nail cosmetic composition in an amount of 2.1% to 10.5% by weight (dry), more preferably 6% to 8% by weight (dry). The use of too small an amount of nitrocellulose tends to unpreferably result in the coated films which are easily damaged. Contrary to this, the use of too large an amount of the nitrocellulose tends to unpreferably result in the too hard and inflexible coated films, which easily cause the undesirable peeling of the coated films.

The resins usable in the present invention are those which are generally used in conventional nail enamels. Examples of such resins are synthetic resins such as alkyd type resins, acryl type resins, toluenesulfonamide type resins, and natural resins such as rosin and shellac. These resins can be used alone or in any mixture thereof.

These resins are generally used in an amount of 3% to 15% by weight, preferably 5% to 12% by weight, based on the total weight of the nail cosmetic compositions. The use of too small an amount of the resin tends to unpreferably result in the coated films which are easily peeled with the elapse of time. Contrary to this, the use of too large an amount of the resin also tends to unpreferably result in the coated films which are easily peeled with the elapse of time.

The plasticizers usable in the nail cosmetic composition of the present invention are those generally used in conventional nail cosmetic compositions. Examples of such plasticizers are phthalate-type plasticizers such as dibutyl phthalate and dioctyl phthalate; citrate-type plasticizers such as tributyl citrate and acetyl tributyl citrate; and camphor. These plasticizers can be used alone or in any mixture thereof.

The plasticizers is generally formulated into the present nail cosmetic composition in an amount of 2% to 8% by weight, preferably 4% to 6% by weight. The use of too small an amount of the plasticizer tends to unpreferably result in the too hard and inflexible coated films which easily cause the undesirable peeling of the coated film. Contrary to this, the use of too large an amount of the plasticizer tends to unpreferably result in the too flexible coated films, which cause the decrease in the appearance with the elapse of time by the effects of various daily actions.

The solvents usable in the nail cosmetic composition of the present invention are those generally used in conventional nail cosmetic compositions. Examples of such solvents are esters such as ethyl acetate, butyl acetate, and cellosolve acetate; alcohols such as ethyl alcohol, isopropyl alcohol, and butyl alcohol; and aromatic hydrocarbons such as toluene. These solvents can be used alone or in any mixture thereof.

The solvent can be, generally, formulated into the present nail cosmetic composition in an amount of 60% to 85% by weight.

The matting agent usable in the nail cosmetic composition of the present invention is silica having an average particle size of 0.01 to 30 μm, preferably 0.5 to 10 μm. When the average size of the silica is less than 0.01 μm, the desired mat finish cannot be obtained. Contrary to this, when the average size of the silica is more than 30 μm, the visual appearance of the coated film is impaired and the desired mat finish effect is not fully effected.

The silica is generally formulated into the nail cosmetic composition of the present invention in an amount of 1% to 10% by weight, preferably 4% to 6% by weight. The use of too small an amount of the silica cannot result in the desired mat finish. Conversely the use of too large an amount of the silica unpreferably increases the viscosity of the resultant nail cosmetic composition thereby causing the poor coatability and a poor storage stability of the composition with the elapse of time. There are no critical limitations to the shape of the silica as long as the average size is within the above-specified range. Also, the silica usable in the present invention can be produced by any production process, including a so-called wet process or dry method. Examples of commercially available silica usable in the present invention are Carplex #67 (particle size=5 μm, Trademark, Shionogi Seiyaku K.K., Japan), Siloid 65 (average particle size=4 μm, Trademark, Fuji Davison Kagaku K.K., Japan), and Siloid 244 (particle size=10 μm, Trade mark, Fuji Davison Kagaku K.K., Japan).

The mica usable in the present nail cosmetic composition is that having the form of a leaf with a thickness of 0.05 to 1.5 μm, preferably 0.05 to 0.1 μm, and has an average particle size of 1 to 30 μm, preferably 3 to 30 μm. The use of a too thin mica is not preferably because such mica is not easily available, whereas the use of mica having a thickness of more than 1.5 μm tends not to sufficiently improve the desired peeling resistance. Furthermore, the use of the mica having too small a diameter tends not to sufficiently act as a filler in the nail cosmetic composition, whereas the use of mica having too large a diameter tends to unpreferably impair the visual appearance of the coated film.

The mica is generally formulated into the nail cosmetic composition of the present invention in an amount of 0.1% to 2.5% by weight, preferably 0.3% to 2.0% by weight. The use of too small an amount of the mica tends not to sufficiently improve the peeling resistance, whereas the use of too large an amount of the mica unpreferably tends to result in the composition which cannot be smoothly applied to the nails.

The nail cosmetic composition according to the present invention may optionally contain any ingredient generally used in conventional nail cosmetic compositions, as long as the desired objects of the present invention are not adversely affected. Examples of such typical optional ingredients are pigments. Typical pigments usable in the present invention are inorganic pigments such as iron oxide (red), iron oxide (yellow), iron oxide (black), and titanium dioxide and organic pigments such as Yellow #4, Red #266, Red #202, and Red #204. These pigments may be preferably formulated into the nail cosmetic composition of the present invention in an amount of 0.1% to 5% by weight.

Examples of other optional ingredients usable in the present invention are perfumes, dyes, pharmaceutically active agents, thickening agent, humectants, and UV absorbers, as long as the desired objects of the present invention are not adversely affected.

A coated film of the nail cosmetic composition according to the present invention has an excellent mat finish and peeling resistance, in addition to the other characteristics required for nail cosmetic compositions such as easy coatability, good durability, water resistance, and oil resistance of the coated film and easy removal with a remover.

EXAMPLE

The present invention will be further explained by, but is by no means limited to, the following Examples and Comparative Examples. Percentages in the formulation amounts of the Examples and Comparative Examples are by weight unless otherwise specified.

Example 1 and Comparative Examples 1 to 5

The nail enamel compositions containing the ingredients listed in Table 1 were prepared as follows. That is, the starting nitrocellulose RS ¼ sec, alkyd resin, acetyltributyl citrate, ethyl acetate, butyl acetate, and isopropyl alcohol were mixed until dissolved, and the talc, kaoline, calcium phosphate, calcium carbonate, mica, pigment, and organophilic bentonite gelling agent were added and the resultant mixture was mixed while agitating.

Thus, the desired nail enamel compositions were prepared.

TABLE 1

| Ingredient | Example 1 | Comparative Example 1 | 2 | 3 | 4 | 5 |
| --- | --- | --- | --- | --- | --- | --- |
| (1) Talc | — | — | 1.5 | — | — | — |
| (2) Kaolin | — | — | — | 1.5 | — | — |
| (3) Calcium phosphate | — | — | — | — | 1.5 | — |
| (4) Calcium carbonate | — | — | — | — | — | 1.5 |
| (5) Mica (thickness = 0.05–0.2 μm, particle size = 1–10 μm) | 1.5 | — | — | — | — | — |
| (6) Nitrocellulose (RS ¼ sec) (30% IPA) | 12 | 12 | 12 | 12 | 12 | 12 |
| (7) Alkyd resin | 10 | 10 | 10 | 10 | 10 | 10 |
| (8) Acetyltributyl citrate | 5 | 5 | 5 | 5 | 5 | 5 |
| (9) Ethyl acetate | 20 | 20 | 20 | 20 | 20 | 20 |
| (10) Butyl acetate | 38 | 38 | 38 | 38 | 38 | 38 |
| (11) Isopropyl alcohol | 6 | 6 | 6 | 6 | 6 | 6 |
| (12) Pigment (lithol rubin BCA/ TiO$_2$ = 4/1) | 1.5 | 1.5 | 1.5 | 1.5 | 1.5 | 1.5 |
| (13) Organophilic bentonite gelling agent | 1 | 1 | 1 | 1 | 1 | 1 |
| (14) Silica | 5 | 5 | 5 | 5 | 5 | 5 |

(Evaluation)

The nail enamel compositions obtained above were evaluated in actual use tests as follows.

The nail enamel composition was packed into a 10 ml glass bottle having an application brush, and the coatability, mat finish, peeling resistance (I) (i.e., application test) and (II) (i.e., cross-cut test) thereof were evaluated. The term "peeling resistance" used herein refers to the degree of peeling of the coated film of the nail enamel composition after application and with the elapse of time (1) Actual Use Test 1 (i.e., Coatability or applicability to nails)
- ○: Easy to apply with clean and smooth coating
- Δ: Not easy to apply
- x: Difficult to apply (2) Actual Use Test 2 (i.e., Mat finish)
- ○: Excellent mat finish
- Δ: Fair mat finish
- x: No mat finish (3) Actual Use Test 3 (i.e., Peeling resistance I)

The peeling resistance of the sample compositions were organoleptically evaluated for each sample by using a panel composed of 10 female members. The sample was applied to 100 nails of the 10 women and left for 3 days. After 3 days, the length of film peelings from the tips of the nails was measured. The results were averaged and evaluated according to the following criteria, based on the average peeling length per one nail.
- ○: Peeling length of 0.5 to 1.0 mm
- Δ: Peeling length of 1.1 to 1.5 mm
- x: Peeling length of more than 1.5 mm (4) Actual Use Test 4 (i.e., Peeling resistance II)

The sample compositions were uniformly coated on glass plates and were dried at room temperature for 12 hours. Thus, dry nail enamel films having a thickness of 20 μm were obtained. The peeling resistances of the films were evaluated according to a cross-cut test generally used for the evaluation of adhesiveness in coating compositions. Thus, the coated films were longitudinally and latitudinally cut to form 100 squares each having a size of 1 mm×1 mm. The results were determined as follows.
- ○: Squares formed after cutting had regular, clean-cut edges
- Δ: Squares formed after cutting were somewhat distorted
- x: Squares formed after cutting had jagged edges The results are as shown in Table 2.

TABLE 2

| Items | Example 1 | Comparative Example 1 | 2 | 3 | 4 | 5 |
|---|---|---|---|---|---|---|
| Coatability | o | o | o | o | o | o |
| Mat finish | o | o | o | o | o | o |
| Peeling resistance (I) | o | x | Δ | x | x | x |
| Peeling resistance (II) | o | x | Δ | x | x | x |

As is clear from the results shown in Table 2, the nail enamel composition of Example 1 had an excellent coatability, mat finish, and peeling resistance. Contrary to this, the nail enamel compositions of Comparative Examples 1 to 5 had a similar coatability and mat finish, but poor peeling resistance when compared with the nail enamel composition of Example 1. Thus, there are remarkable differences between the present nail enamel composition and the comparative nail enamel compositions. The coated films of the comparative nail enamel compositions were easily peeled with the elapse of time after application and had a poor durability.

Examples 2 to 5 and Comparative Example 6 to 10

The nail cosmetic compositions containing the ingredients listed in Table 3 were prepared as follows.

The starting nitrocellulose RS ¼ sec, alkyd resin, acetyl tributyl citrate, ethyl citrate, butyl acetate, and isopropyl alcohol were until dissolved, and the mica, pigment and organophylic bentonite gelling agent were added and the resultant mixture was mixed while agitating.

Thus, the nail enamel compositions of Examples 2 to 4 and Comparative Examples 6 to 10 as well as the nail enamel overcoat of Example 5 were prepared.

TABLE 3

| Ingredient | Example 2 | 3 | 4 | 5 | Comparative Example 6 | 7 | 8 | 9 | 10 |
|---|---|---|---|---|---|---|---|---|---|
| (1) Nitrocellulose (RS ¼ sec) (30% IPA) | 12 | 12 | 12 | 12 | 12 | 12 | 12 | 12 | 12 |
| (2) Alkyd resin | 10 | 10 | 10 | 10 | 10 | 10 | — | — | — |
| (3) Sulronamide resin | — | — | — | 10 | — | — | 10 | 10 | 10 |
| (4) Acetyltributyl citrate | 5 | 5 | 5 | 5 | 5 | 5 | 5 | 5 | 5 |
| (5) Ethyl acetate | 20 | 20 | 20 | 20 | 20 | 20 | 20 | 20 | 20 |
| (6) Butyl acetate | 38 | 37.5 | 37 | 30.9 | 39.45 | 36.5 | 38 | 38 | 37.5 |
| (7) Isopropyl alcohol | 6 | 6 | 6 | 6 | 6 | 6 | 6 | 6 | 6 |
| (8) Pigment (lithol rubin BCA/TiO$_2$ = 4/1) | 1.5 | 1.5 | 1.5 | — | 1.5 | 1.5 | 1.5 | 1.5 | 1.5 |
| (9) Organophilic bentonite gelling agent | 1 | 1 | 1 | 1 | 1 | 1 | 1 | 1 | 1 |
| (10) Mica (amount) | 1.5 | 2.0 | 2.5 | 0.1 | 0.05 | 3 | 1.5 | 1.5 | 2.0 |
| Thickness (μm) | 0.05 | 0.1 | 1.5 | 0.1 | 0.1 | 0.05 | 2 | 0.1 | 0.1 |
| Particle size (μm) | 1 | 10 | 10 | 1 | 3 | 3 | 3 | 50 | 0.5 |
| (11) Silica (amount) (size 1 μm) | 5 | 5 | 5 | 5 | 5 | 5 | 5 | 5 | 5 |

The nail cosmetic compositions of Examples 2 to 5 and Comparative Examples 6 to 10 were evaluated in the same manner as in Example 1. The results are as shown in Table 4.

TABLE 4

| Item | Example 2 | 3 | 4 | 5 | Comparative Example 6 | 7 | 8 | 9 | 10 |
|---|---|---|---|---|---|---|---|---|---|
| Coatability | o | o | o | o | o | x | o | o | o |
| Mat finish | o | o | o | o | o | o | o | o | o |
| Peel resistance I | o | o | Δ | o | x | o | x | x | x |
| Peel resistance II | o | o | Δ | o | x | o | x | x | x |

TABLE 4-continued

| Item | Example | | | | Comparative Example | | | | |
|---|---|---|---|---|---|---|---|---|---|
| | 2 | 3 | 4 | 5 | 6 | 7 | 8 | 9 | 10 |
| Visual appearance*1 | o | o | o | o | o | o | o | x | o |

*1The appearance of the coated film was visually evaluated.
o ... Good
Δ ... Fair
x ... Poor As is clear from the results shown in Table 4, the nail cosmetic compositions of Examples 2 and 3 had an excellent coatability, mat finish, and peeling resistance. In the case of Example 4, since the thickness of the mica is relatively thick, i.e., 1.5 μm, the peeling resistance of the coated film was somewhat weak when compared to Examples 2 and 3, although it is still acceptable. Contrary to this, in the case of the Comparative Examples, the coated film was easily peeled when the amount of the mica was too small (see Comparative Example 6), the coatability was inferior when the amount of mica was too large (see Comparative Example 7), the coated film was easily to peeled when the mica was too thick (see Comparative Example 8), the visual appearance of the coated enamel film was poor when the particle size of the mica was too large (see Comparative Example 9), and the coated film was easily peeled when the particle size of the mica was too small (see Comparative Example 10).

The enamel basecoat composition of Example 5, which can be used over the mat finish or conventional nail enamel coat, had an excellent coatability, mat finish, peeling resistance, and visual appearance.

We claim:

1. A nail cosmetic consisting essentially of 3% to 15% by weight of nitrocellulose, 3% to 15% by weight of a resin, 2% to 8% by weight of a plasticizer, 60% to 85% by weight of at least one solvent selected from the group consisting of esters, alcohols, are aromatic hydrocarbons, 1% to 10% by weight of, as a matting agent, silica having an average particle size of 0.01 to to 30 μm, and 0.1% to 2.5% by weight of mica in the form of a leaf having a thickness of 0.05 to 1.5 μm and a particle size of 1 to 30 μm.

* * * * *